US00PP18705P2

(12) United States Plant Patent
Bradford

(10) Patent No.: US PP18,705 P2
(45) Date of Patent: Apr. 1, 2008

(54) PLUM TREE NAMED 'PLUMGIANT I'

(50) Latin Name: *Prunus salicina*
Varietal Denomination: Plumgiant I

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,895

(22) Filed: Dec. 7, 2006

(51) Int. Cl.
*A01H 5/00* (2006.01)

(52) U.S. Cl. ..... Plt./184
(58) Field of Classification Search ..... Plt./184
See application file for complete search history.

(56) References Cited

U.S. PATENT DOCUMENTS

PP14,220 P2 10/2003 Bradford
PP14,247 P2 10/2003 Bradford

*Primary Examiner*—Kent Bell
*Assistant Examiner*—S. B. McCormick-Ewoldt

(57) ABSTRACT

The present invention relates to a plum tree and more particularly to a new and distinct variety broadly characterized by a medium size, vigorous, hardy, and productive tree that is self-unfruitful and requires cross-pollination. The fruit matures under the ecological conditions described during early August, with first picking on Aug. 3, 2006. The fruit is uniformly giant in size, almost black in skin color, clingstone in type, nearly globose in shape, very light yellow to white in flesh color, firm in texture, and very sweet in flavor.

1 Drawing Sheet

Botanical classification: *Prunus salicina.*
Varietal denomination: 'Plumgiant I'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of plum tree, which has been denominated varietally as 'Plumgiant I'.

During a typical blooming season I isolate as seed parents both individual and groups of different plum trees by covering them with screen houses. A hive of bees is placed inside each such house, and bouquets to provide pollen from different plum trees are placed in buckets near the trees approximately every two days for the duration of the bloom. During 2000 one such house containing several unnamed plums was crossed by me in this manner. Upon reaching maturity the fruit from these plum trees was harvested and the seeds were removed, cracked, stratified and germinated as a group with the label "H842P". They were grown as seedlings on their own root is my greenhouse and upon reaching dormancy transplanted to a cultivated area of my experimental orchard located near Le Grand, Calif. in Merced County (San Joaquin Valley). During the summer of 2003 the present variety was selected by me as a single plant from the group of seedlings described above. Subsequent to origination of the present variety of plum tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'August Yummy' (U.S. Plant Pat. No. 14,247) plum by being self-unfruitful and by producing fruit that matures in August, that is sweet in flavor, and that is clingstone in type, but is distinguished therefrom by producing fruit that is very light yellow to white in flesh color, almost black in skin color, larger in size, and matures about seven days earlier.

SUMMARY OF VARIETY

The present plum variety is characterized by a medium size, vigorous, hardy, and productive tree. Being self-unfruitful, the present variety requires cross pollination from a plum that blooms during the mid season, such as 'September Yummy' (U.S. Plant Pat. No. 14,220). The fruit matures under the ecological conditions described during early August, with first picking on Aug. 3, 2006. The fruit is uniformly giant in size, almost black in skin color, clingstone in type, nearly globose in shape, very light yellow to white in flesh color, firm in texture, and very sweet in flavor.

DRAWING

The accompanying photograph consists of four whole fruits positioned to display the characteristics of the skin color and form, one fruit divided transversely to the suture plane to reveal the flesh and stone, typical leaves, insets depicting the buds and blossoms as they appear on the tree, and a tip shoot.

DETAILED BOTANICAL DESCRIPTION

Referring now more specifically to the pomological characteristics of this new and distinct variety of plum tree, the following has been observed under the ecological conditions prevailing near Le Grand, Merced County (San Joaquin Valley), Calif. The fruit description was developed at the state of full ripe on Aug. 12, 2006, on the original tree during its sixth growing season. The flower and bud descriptions were developed during the previous blooming season. All major color code designations are by reference to the Inter-Society Color Council, National Bureau of Standards. Common color names are also used occasionally.

Parentage:
*Seed parent.*—Unnamed black plum.
*Pollen parent.*—Unknown.

Tree

Size: Medium, reaching and maintaining a height of 10' [3.05 m.] and a spread of 7' [2.13 m.] after six growing seasons utilizing typical dormant pruning.
Vigor: Vigorous, responding typically to irrigation and fertilization. The variety grows about 4' [1.22 m.] of surplus top-growth during the spring and summer. The plant should be grown on a standard commercial rootstock for production purposes.
Growth: Upright and dense.
Form: Pruned to a vase form.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Very productive, thinning usually necessary.
Fertility: Self-unfruitful, requiring cross pollination by a suitable mid seasonal blooming plum such as 'September Yummy' (U.S. Plant Pat. No. 14,220).
Bearing: Regular bearer, with no crop failures observed.
Trunk:
*Size.*—Medium, reaching a maximum diameter of 4¾" [121 mm.] after the sixth growing season.
*Texture.*—Shaggy.
*Bark color.*—A Dark grayish reddish brown [47. d.gy.rBr] and Deep brown [56. deep Br] variegation with Moderate yellowish brown [77. m.yBr] crevices present.
*Lenticels.*—Approximate Number Per Square Inch: 6. Color: Deep orange yellow [69. deep OY]. Typical Size: ⅛" [3.2 mm.] to ⅜" [9.5 mm.]. Shape: Eye-shaped to elongated.
Branches:
*Size.*—Diameter of limb is 2¾" [70 mm.] measured 12" above the crotch, 1⅜" [35 mm.] measured 12" above the first fork.
*Texture.*—Smooth on first and second year wood, increasing roughness with age.
*Color.*—1st Year Wood Topside: Deep yellowish brown [75. deep yBr]. 1st Year Wood Underside: Brilliant yellow green [116. brill.YG]. Older Wood: Strong yellowish brown [74. s.yBr].
*Lenticels.*—Number Per Square Inch: More than 50 on second year wood. Color: Light yellowish brown [76. l.yBr]. Typical size: 1/64" [0.4 mm.] to 3/32" [2.4 mm.]. Shape: Elongated.
Leaves:
*Size.*—Large. Average Length: 5" [127 mm.]. Average width: 2⅛" [54 mm.].
*Arrangement.*—Alternate.
*Thickness.*—Medium.
*Form.*—Elliptical.
*Apex.*—Acuminate.
*Base.*—Acute with an average angle base of 75 degrees.
*Surface.*—Smooth.
*Color.*—Dorsal Surface: Moderate olive green [125. m.OlG]. Ventral Surface: Moderate yellow green [120. m.YG].
*Margin.*—Finely serrate.
*Venation.*—Pinnately net veined.
*Petiole.*—Average Length: ½" [12.7 mm.]. Average Thickness: 5/64" [2.0 mm.]. Color: Light yellow green [119. l.YG].
*Stipules.*—Number: 2 per leaf, up to 6 per growing tip. Average Length: ⅜" [9.5 mm.]. Color: Light yellow green [119. l.YG] becoming Moderate reddish brown [43. m.rBr] with age.
*Glands.*—Number: Mostly 2 per leaf. Position: Alternately positioned at the intersection of the petiole and the leaf blade. Size: Small. Form: Globose. Color: Moderate yellow green [120. m.YG] becoming Dark grayish brown [62. d.gy.Br] with age.
*Leaf buds.*—Pointed, medium.
Flower buds:
*Hardiness.*—Hardy, with respect to central California winters.
*Diameter.*—Typically 3/16" [4.8 mm.] 1 week before bloom.
*Length.*—Typically ⅜" [9.5 mm.] 1 week before bloom.
*Form.*—Not appressed.
*Surface.*—Pubescent.
*Color.*—White [263. White].
Flowers: Perfect, complete, perigynous, usually a single pistil, typically twenty-four or more stamens, five sepals and petal locations alternately positioned.
*Average flower diameter.*—1 1/16" [27.0 mm.].
*Number of petals.*—Five, no double blossoms observed.
*Petal shape.*—Circular to oval.
*Petal margin.*—Smooth.
*Average petal diameter.*—½" [12.7 mm.].
*Average petal length.*—½" [12.7 mm.].
*Petal apex.*—Rounded.
*Petal base.*—Rounded to somewhat obtuse.
*Petal color.*—White [263. White].
*Anther color.*—Pale yellowish pink [31. p.yPk] over a Yellowish white [92. yWhite] center.
*Stigma color.*—Pale yellow green [121. p.YG].
*Sepal color.*—Brilliant yellow green [116. brill.YG] with small areas of Grayish purplish pink [253. gy.pPk].
*Sepal length.*—5/32" [4.0 mm.].
*Sepal width.*—⅛" [3.2 mm.].
*Average pistil length.*—9/16" [14.3 mm.].
*Average stamen length.*—7/16" [11.1 mm.].
*Fragrance.*—Moderate.
*Pollen production.*—Scarce.
*Blooming period.*—Medium, with 'September Yummy' (U.S. Plant Pat. No. 14,220).
*Onset of bloom.*—One percent on Feb. 24, 2006.
*Date of full bloom.*—Mar. 11, 2006.
*Duration of bloom.*—One to two weeks, dependent on ambient temperature.
*Bloom density.*—Very heavy.
*Number per cluster.*—2 to 10, average 5.

FRUIT

Maturity when described: Full ripe, Aug. 12, 2006.
Date of first picking: Aug. 3, 2006.
Date of last picking: Aug. 15, 2006.
Size: Uniform, very large.

*Average diameter axially.*—2⅝" [66.7 mm.].
*Average diameter across cheek plane.*—3" [76.2 mm.].
*Average diameter across suture plane.*—3" [76.2 mm.].
*Typical weight.*—7.5 ounces [213 grams].

Form: Uniform, usually symmetrical, globose.
*Longitudinal section form.*—Round to elliptical.
*Axial view.*—Round.

Suture: An inconspicuous black line located in shallow groove extending from the base to apex.

Ventral surface: Rounded, lipped slightly toward the base.

Lips: Fairly equal.

Cavity: Flaring, circular to slightly elongated in the suture plane, suture showing on one side, Deep reddish brown [41. deep rBr] stem markings on less than half.
*Depth.*—⅝" [15.9 mm.].
*Breadth.*—1⅛" [28.6 mm.].

Base: Truncate, cordate if viewed parallel to suture.

Apex: Rounded with a very slight hump at the pistil point.

Pistil point: An inconspicuous dot.

Stem: Medium.
*Average length.*—7/16" [11.1 mm.].
*Average width.*—⅛" [3.2 mm.].

Skin:
*Thickness.*—Medium.
*Surface.*—Smooth.
*Tenacity.*—Tenacious to flesh.
*Taste.*—Astringent.
*Tendency to crack.*—Slight.
*Color.*—Brownish black [65. brBlack] over a Very dark red [17. v.d.R] background with virtually no freckling.
*Bloom.*—Moderate.

Flesh:
*Color.*—Yellowish white [92. yWhite] near the skin, Pale yellow [89. p.Y] near the stone.
*Surface of pit cavity.*—Moderate yellow [87. m.Y] broken fibers when twisted away from stone.
*Amygdalin.*—Moderate.
*Juice.*—Abundant, rich.
*Texture.*—Firm, tough.
*Fibers.*—Abundant, fine.
*Ripens.*—A little earlier toward the apex.
*Flavor.*—Acidic and sweet, typically 18-20 brix.
*Aroma.*—Very slight.
*Eating quality.*—Very good.

STONE

Type: Clingstone.

Form: Oval.

Hilum: Narrow.

Base: Oblique.

Apex: Rounded to obtuse with a very small but very sharp tip.

Sides: Equal.

Surface: Rough throughout, with characteristic vertical ridges running from the base to mid section and a typical groove along the dorsal fin.

External color of stone: Light yellowish brown [76. l.yBr].

Pit wall color when cracked: Light yellowish brown [76. l.yBr].

Cavity surface color: Deep brown [56. deep Br].

Average pit wall thickness: 1/16" [1.6 mm.].

Average width: ¾" [19.1 mm.].

Average length: 1" [25.4 mm.].

Average breadth: 7/16" [11.1 mm.].

Tendency to split: Slight.

Kernel:
*Form.*—Oval.
*Skin color.*—Dark orange yellow [72. d.OY].
*Pellicle color.*—Moderate brown [58. m.Br].
*Vein color.*—Moderate brown [58. m.Br].
*Taste.*—Bitter.
*Viable.*—Yes.
*Average width.*—½" [12.7 mm.].
*Average length.*—9/16" [14.3 mm.].
*Amygdalin.*—Abundant.

USE

Market: Fresh market and long distance shipping.

Keeping quality: Good, fruit quality observed to remain in good condition after 21 days in standard cold room at 36° Fahrenheit [2° Celsius].

Shipping quality: Good.

Resistance to insects: No unusual susceptibilities noted.

Resistance to diseases: No unusual susceptibilities noted.

Resistance to heat: Damage observed to some fruit following extended period of temperatures in excess of 110 degrees Fahrenheit during the 2006 season, none observed during the 2005 season.

Other Notes

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, substantially as illustrated and described, that is most similar to 'August Yummy' (U.S. Plant Pat. No. 14,247) plum by being self-unfruitful and by producing fruit that matures in August, that is sweet in flavor, and that is clingstone in type, but is distinguished therefrom by producing fruit that is very light yellow to white in flesh color, almost black in skin color, larger in size, and matures about seven days earlier.

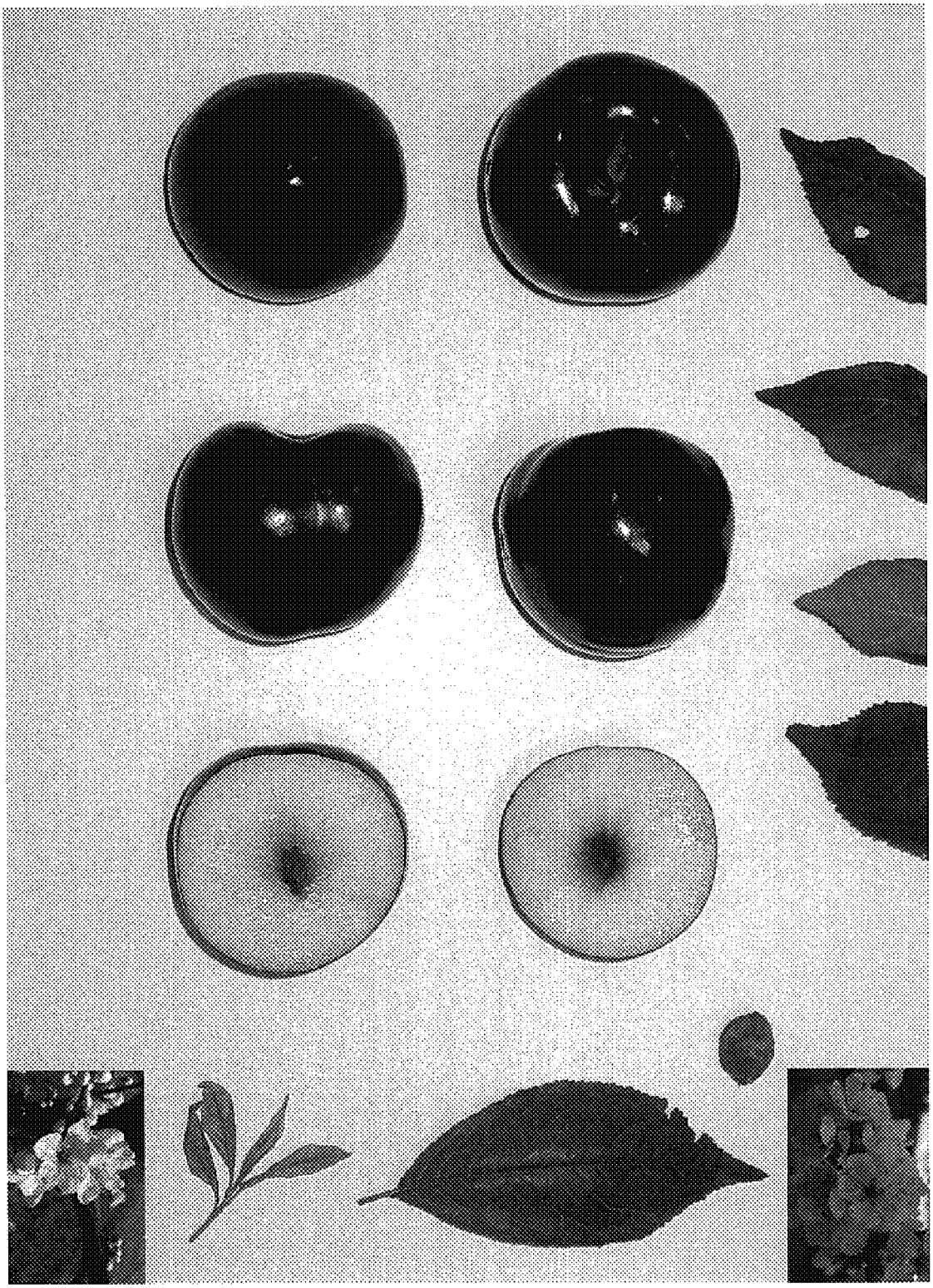

* * * * *